(12) United States Patent
Lee et al.

(10) Patent No.: US 8,374,989 B2
(45) Date of Patent: Feb. 12, 2013

(54) SYSTEM FOR CUSTOMIZED PREDICTION OF MENSTRUATION PERIOD OR FERTILITY PERIOD AND CALCULATION METHOD THEREFOR

(75) Inventors: Jin Won Lee, Seoul (KR); Wang Yun Won, Gyeonggi-do (KR); Kwang-Soon Lee, Seoul (KR)

(73) Assignee: Industry-University Cooperation Foundation Sogang University, Seoul (KR)

( * ) Notice: Subject to any disclaimer, the term of this patent is extended or adjusted under 35 U.S.C. 154(b) by 681 days.

(21) Appl. No.: 12/579,831

(22) Filed: Oct. 15, 2009

(65) Prior Publication Data
US 2010/0191696 A1 Jul. 29, 2010

(30) Foreign Application Priority Data
Jan. 23, 2009 (KR) ........................ 10-2009-0005819

(51) Int. Cl.
*G06N 7/02* (2006.01)
*G06N 7/06* (2006.01)

(52) U.S. Cl. ........................ 706/52; 514/171; 600/551

(58) Field of Classification Search .................... None
See application file for complete search history.

(56) References Cited

U.S. PATENT DOCUMENTS

| | | | | |
|---|---|---|---|---|
| 5,685,319 A | * | 11/1997 | Marett | 600/551 |
| 2003/0150961 A1 | * | 8/2003 | Boelitz et al. | 244/172 |
| 2009/0326410 A1 | * | 12/2009 | James et al. | 600/551 |

* cited by examiner

*Primary Examiner* — Kakali Chaki
*Assistant Examiner* — Kalpana Bharadwaj
(74) *Attorney, Agent, or Firm* — Alston & Bird LLP

(57) ABSTRACT

A system for customized prediction of a menstruation period or a fertility period is provided. The system includes a vital information measurer for measuring vital information about a user, a basic menstruation information generator for calculating the first day of menstruation or an ovulation day using the vital information received from the vital information measurer and outputting the first day of menstruation or the ovulation day as basic menstruation information, a menstruation cycle modeler having a menstruation cycle model representing a menstruation cycle as a function with a predetermined period, and a model parameter estimator for estimating and compensating a menstruation cycle parameter of the menstruation cycle model using the basic menstruation information received from the basic menstruation information generator.

11 Claims, 3 Drawing Sheets

SYSTEM FOR CUSTOMIZED PREDICTION OF MENSTRUATION PERIOD OR FERTILITY PERIOD AND CALCULATION METHOD THEREFOR

CROSS-REFERENCE TO RELATED PATENT APPLICATION

This application claims the benefit under 35 U.S.C. §119(a) of a Korean Patent Application filed in the Korean Intellectual Property Office on Jan. 23, 2009 and assigned Serial No. 10-2009-0005819, the entire disclosure of which is hereby incorporated by reference.

BACKGROUND OF THE INVENTION

1. Field of the Invention

The present invention relates to a system for customized prediction of a menstruation period or a fertility period and a calculation method therefor. More particularly, the present invention relates to an apparatus for customized calculation of a menstruation period or a fertility period in order to provide accurate information that best matches the current state of an individual and a providing method thereof.

2. Description of the Related Art

Every month, an ovum or egg is released from one of the two ovaries of a female body. To prepare for implantation of an egg fertilized with a sperm into the uterus, the endometrium softens and thickens. Without the fertilization, the thickened endometrium breaks down because it is not needed. The resulting physiological phenomenon of discharging menstruation blood and the expelled endometrium outside the vagina is called menstruation (or menses). Menstruation occurs in normal mature women. A menstruation cycle lasts for 26 to 32 days and has three to five days of bleeding.

Because menstruation adversely affects women's daily activities, the menstruation cycle is widely used to protect female workers in working places as well as their personal lives. Family planning, i.e. planning the number of children or birth spacing, is required to live a happy family life and can be made by predicting an ovulation day and a fertility period based on a menstruation cycle.

Typically, a menstruation period or a fertility period is calculated from the onset of the last menstruation, on the assumption of a menstruation cycle of 28 days. That is, assuming that ovulation and menstruation occur every 28 days, the next menstruation period or fertility period is predicted from the first day of the previous menstruation.

Menstruation cycles vary in individuals. A woman's menstruation cycle continues to change because it is significantly affected by factors including the environment in which she lives. Therefore, it is difficult to predict a menstruation period and a fertility period based on the menstruation cycle of 28 days. For example, there is a possibility that a woman may be pregnant in spite of her natural birth control based on her calculation of a fertility period from the first day of the last menstruation.

In another example, although a woman has predicted her next menstruation period from the first day of the last menstruation and planned her overseas travel, unexpected menstruation makes her unpleasant during the travel.

Few specified organized services are known to measure an individual woman's menstruation cycle and predict her menstruation period or fertility period using the menstruation cycle through a portable terminal such as a mobile terminal.

Accordingly, there exists a need for a system for customized prediction of a menstruation period or a fertility period that best matches an individual woman's current status by correcting a conventional menstruation or fertility calculation method, for active utilization of a menstruation period in individuals' daily lives including family planning and in working places. Also, a more accurate measurement of the first day of menstruation and an ovulation day is required for the accurate prediction of the menstruation period or the fertility period. An apparatus for acquiring such information in an easy manner to receive a high-quality service along with other services and a method for providing the high-quality service are also needed.

SUMMARY OF THE INVENTION

An aspect of exemplary embodiments of the present invention is to address at least the problems and/or disadvantages and to provide at least the advantages described below. Accordingly, an aspect of exemplary embodiments of the present invention is to provide: a customized system for calculating the first day of menstruation and an ovulation day based on measured vital information about a user, such as hormone levels, temperature, etc. or receiving the first menstruation day directly from the user, estimating a parameter of a menstruation cycle model expressed as a function of a certain period using the calculated first menstruation day or ovulation day, or the directly received first menstruation day, and predicting a menstruation period or a fertility period that best matches the current status of the user; and a calculation method therefor.

Another aspect of exemplary embodiments of the present invention provides: a system for facilitating measurement of an individual woman's menstruation cycle, accurately predicting her menstruation period or fertility period based on the menstruation cycle, and servicing the predicted menstruation period or fertility period by applying a developed technology to a portable terminal such as a mobile terminal; and a calculation method therefor.

In accordance with an aspect of exemplary embodiments of the present invention, there is provided a system for customized prediction of a menstruation period or a fertility period, including: a vital information measurer for measuring vital information about a user; a basic menstruation information generator for calculating the first day of menstruation or an ovulation day using the vital information received from the vital information measurer and outputting the first day of menstruation or the ovulation day as basic menstruation information; a menstruation cycle modeler for representing a menstruation cycle as a function with a predetermined period; and a model parameter estimator for estimating and compensating a menstruation cycle parameter of the menstruation cycle model using the basic menstruation information received from the basic menstruation information generator.

The system may further include a linearizer for linearing a non-linear menstruation cycle model of the menstruation cycle modeler and outputting the linearized menstruation cycle model to the model parameter estimator, and the vital information measurer may include a sensor for measuring a variation in one of blood, sweat, and temperature of the user.

In accordance with another aspect of exemplary embodiments of the present invention, there is provided a mobile terminal having a power supply, an input portion, an operator and a display, including a system for customized prediction of a menstruation period or a fertility period. The system includes a vital information measurer for measuring vital information about a user, a basic menstruation information generator for calculating the first day of menstruation or an ovulation day using the vital information received from the vital information measurer and outputting the first day of menstruation or the ovulation day as basic menstruation information, a menstruation cycle modeler for representing a menstruation cycle as a function with a predetermined period, and a model parameter estimator for estimating and compensating a menstruation cycle parameter of the menstruation cycle model using the basic menstruation information received from the basic menstruation information generator.

The system may further include a linearizer for linearing a non-linear menstruation cycle model of the menstruation cycle modeler and outputting the linearized menstruation cycle model to the model parameter estimator, and the vital information measurer may include a sensor for measuring a variation in one of blood, sweat, and temperature of the user.

In accordance with a further aspect of exemplary embodiments of the present invention, there is provided a method for customized calculation of a menstruation period or a fertility period, including: measuring vital information about a user by a vital information measurer; calculating the first day of menstruation or an ovulation day using the vital information received from the vital information measurer and outputting the first day of menstruation or the ovulation day as basic menstruation information; estimating a model parameter indicating a menstruation cycle in a menstruation cycle model represented as a function with a predetermined period using the basic menstruation information by a model parameter estimator, and calculating a menstruation period or a fertility period of the user using the estimated model parameter by a menstruation cycle modeler.

The model parameter may be estimated by the Newton-Raphson method and the Newton-Raphson method may use the following model parameter estimation equation:

$$\hat{T} = \operatorname{argmin} \sum_{k=1}^{N} \beta(k) [f(T; t_k) - \hat{f}(\hat{T}; t_k)]^2$$

subject to $\hat{T}_{min} \le \hat{T} \le \hat{T}_{max}$ where $\hat{T}$ denotes the parameter representing a menstruation cycle, $t_k$ denotes the first day of a $k^{th}$ menstruation or a $k^{th}$ ovulation day, $\hat{f}(\hat{T}; t_k)$ denotes a function value of a periodic function $\hat{f}$ that the menstruation cycle modeler calculates for time $t_k$, and $\beta$ is a forgetting factor.

Also, the model parameter may be estimated using the steepest descent method, and the menstruation cycle of the menstruation cycle model may be estimated based on previously received vital information about the user by the model parameter estimator.

The model parameter may be compensated by the recursive least square estimation method, and the recursive least square estimation method may use the following model parameter compensation equation:

$$\hat{T}(N) = \hat{T}(N-1) + R^{-1}(N)\phi(N)(f(N) - \phi^T(N)\hat{T}(N-1))$$

$$R(N) = \lambda(N)R(N-1) + \phi(N)\phi^T(N)$$

where $$R(N) = \sum_{k=1}^{N} \beta(k)\phi(k)\phi^T(k)$$

where $\hat{T}$ denotes the parameter representing a menstruation cycle, φ denotes a linearized menstruation cycle model, and β is a forgetting factor.

BRIEF DESCRIPTION OF THE DRAWINGS

The above and other objects, features and advantages of certain exemplary embodiments of the present invention will be more apparent from the following detailed description taken in conjunction with the accompanying drawings, in which.

Throughout the drawings, the same drawing reference numerals will be understood to refer to the same elements, features and structures.

DETAILED DESCRIPTION OF EXEMPLARY EMBODIMENTS

The matters defined in the description such as a detailed construction and elements are provided to assist in a comprehensive understanding of exemplary embodiments of the invention. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

According to the present invention, a system for customized prediction of an individual woman's menstruation period or fertility period is provided based on the following known techniques in order to coordinate a menstruation cycle to best match her current status and more accurately calculate the menstruation period or fertility period.

A preferred embodiment of the present invention will be described in detail.

Figure 1:
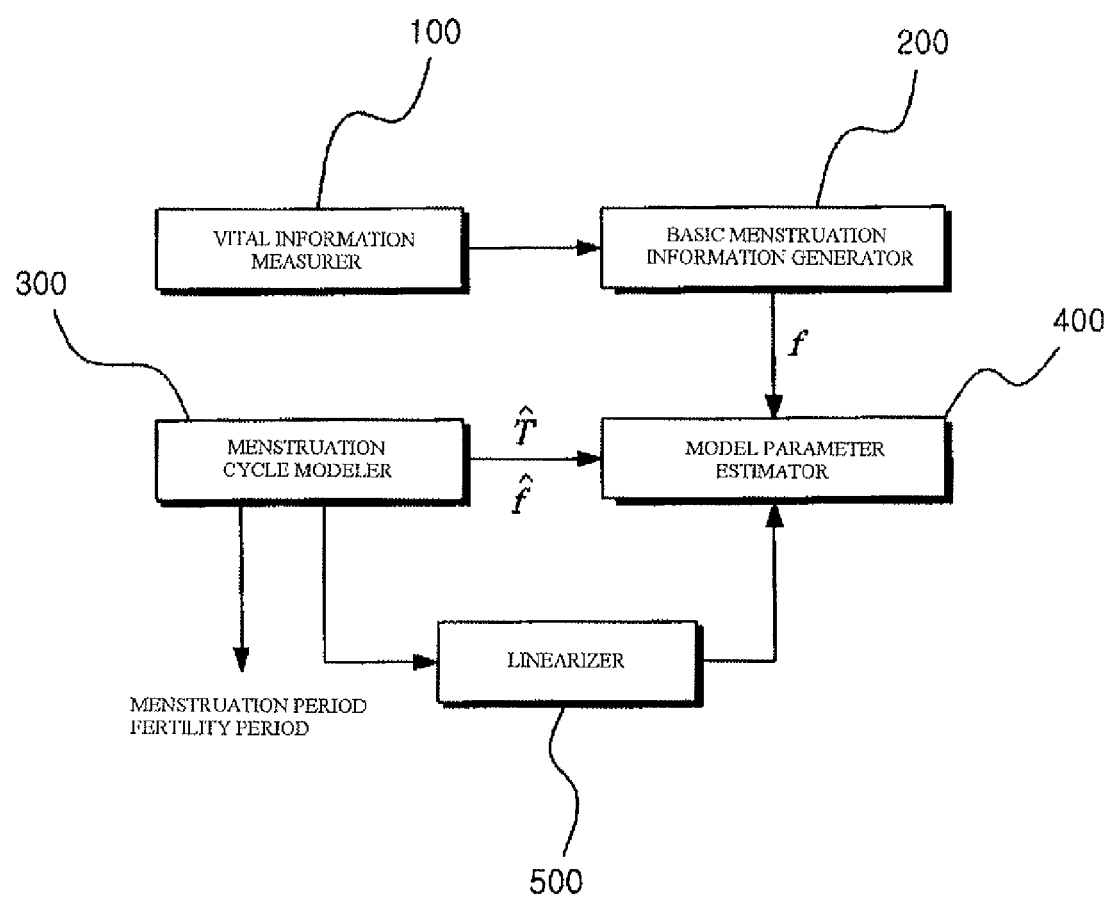
FIG. 1 is a block diagram of a system for customized prediction of a menstruation period or fertility period according to an embodiment of the present invention.

FIG. 1 is a block diagram of a customized menstruation or fertility period prediction system according to an embodiment of the present invention.

Referring to FIG. 1, the customized menstruation or fertility period prediction system includes a vital information measurer 100, a basic menstruation information generator 200, a menstruation cycle modeler 300, a model parameter estimator 400, and a linearizer 500.

The vital information measurer 100 measures vital information including temperature, the levels of hormones related to a menstruation cycle in blood, etc. through a sensor equipped in a terminal. The menstruation cycle-related hormones are estrogen, progesterone, follicle stimulating hormone, luteinzing hormone, etc.

That is, the vital information related to the menstruation cycle may be acquired by measuring variations in hormones from blood, urine, sweat or the like, and measuring a temperature variation through the sensor in the vital information measurer 100.

The basic menstruation information generator 200 calculates the first day of menstruation or an ovulation day using the vital information received from the vital information measurer 100. Alternatively, the basic menstruation information generator 200 receives information indicating the first day of menstruation directly from the user. The first day of menstruation and the ovulation day are calculated based on the idea that the blood hormone levels received from the vital information measurer 100 vary over a woman's menstruation cycle.

Also, the temperature rises 2-3° C. from a basal temperature during the length of the time from ovulation to menstruation. Therefore, like hormones, the first day of menstruation and the ovulation day are calculated using the temperature information having periodicity. The calculated first day of menstruation and the ovulation day are used for calculating a menstruation cycle.

The menstruation cycle modeler 300 has a model representing a menstruation cycle including a menstruation period and a fertility period as a periodic function with a certain period.

The menstruation cycle model satisfies the following equation.

$$\hat{f}(t) = \hat{f}(t - \hat{T}) \quad (1)$$

where $\hat{T}$ denotes a menstruation cycle parameter and t denotes time. $\hat{f}(t)$ denotes a periodic function with a certain period and any of a sine function, a cosine function, etc. is available as $\hat{f}(t)$ as far as it is a periodic function with a certain period. Modeling of the menstruation cycle model is readily understood by those skilled in the art and will not be described below in detail.

The model parameter estimator 400 estimates the menstruation cycle parameter $\hat{T}$ based on information about the first day of menstruation or the ovulation day received from the basic menstruation information generator 200.

An individual's menstruation cycle is significantly affected by her ambient environment and varies in time. The time-varying feature of the menstruation cycle degrades the menstruation and fertilization prediction and calculation performance of the menstruation cycle modeler 300.

In this context, the menstruation cycle model is compensated by estimating the menstruation cycle parameter $\hat{T}$ in the model parameter estimator 400 in an embodiment of the present invention.

Meanwhile, the model parameter estimator 400 functions to estimate and compensate the menstruation cycle parameter $\hat{T}$ within a plurality of constraint conditions, which is expressed as $$\hat{T} = \operatorname{argmin} \sum_{k=1}^{N} \beta(k) \left[ f(T; t_k) - \hat{f}(\hat{T}; t_k) \right]^2 \quad (2)$$

subject to $\hat{T}_{min} \leq \hat{T} \leq \hat{T}_{max}$ where $\hat{T}$ denotes the menstruation cycle parameter, $t_k$ denotes the first day of a $k^{th}$ menstruation or a $k^{th}$ ovulation day (k=1, 2, ... N, and N is the total number of data received from the basic menstruation information generator 200), and $\hat{f}(\hat{T}; t_k)$ denotes the function value of a periodic function $\hat{f}$ that the menstruation cycle modeler 300 calculates and outputs for the input of the menstruation cycle parameter $\hat{T}$ for time $t_k$ from the model parameter estimator 400. $f(T; t_k)$ denotes the function value of a periodic function $f$ with a predetermined cycle T for time $t_k$, as measured by the vital information measurer 100 and received from the basic menstruation information generator 200. $\hat{T}_{max}$ and $\hat{T}_{min}$ are the maximum and minimum values of the menstruation cycle $\hat{T}$, respectively. $\beta$ is a forgetting factor that functions to apply a small weight to past old data and a large weight to recent data during the parameter estimation. The forgetting factor $\beta$ is given as $$\beta(k) = \lambda(k)\beta(k-1) \text{ where } \beta(N)=1, 0 \leq \lambda(k) \leq 1,$$
$$1 \leq k \leq N-1 \quad (3)$$

where $\lambda$ is a parameter ranging from 0 to 1, functioning to apply a small weight to relatively old received data during the parameter estimation.

Meanwhile, the performance of the model parameter estimator 400 may be coordinated by controlling the parameter $\lambda$. The model parameter estimator 400 estimates the parameter $\hat{T}$ of the menstruation cycle model using initially received basic menstruation information (e.g., a first menstruation day or an ovulation day) by equation (2) in the manner that satisfies a given constraint condition. According to an embodiment of the present invention, the Newton-Raphson method is used for the least square estimation described as equation (2).

On the other hand, upon receipt of additional basic menstruation information after estimating the menstruation cycle parameter $\hat{T}$ using the initially received basic menstruation information, the menstruation cycle parameter $\hat{T}$ is compensated by the recursive least square estimation expressed as $$\hat{T}(N) = \hat{T}(N-1) + R^{-1}(N)\phi(N)\left(f(N) - \phi^T(N)\hat{T}(N-1)\right) \quad (4)$$

$$R(N) = \lambda(N)R(N-1) + \phi(N)\phi^T(N)$$

where $$R(N) = \sum_{k=1}^{N} \beta(k)\phi(k)\phi^T(k)$$

where $\phi$ denotes a linearized menstruation cycle model acquired by the linearizer 500. According to an embodiment of the present invention, a compensated parameter $\hat{T}$ for the menstruation cycle model is calculated by substituting the parameter $\hat{T}$ obtained from the least square estimation of equation (2) for $\hat{T}(N-1)$ in equation (4) and substituting the additional basic menstruation information for $f(N)$ in equation (4). That is, the model parameter estimator 400 compensates the parameter $\hat{T}$ of the menstruation cycle model so as to match the compensated parameter $\hat{T}$ to the additional basic menstruation information received from the basic menstruation information generator 200 by the recursive least square estimation of equation (4).

The linearizer 500 linearizes a non-linear menstruation cycle model of the menstruation cycle modeler 300 and outputs the linearized menstruation cycle model to the model parameter estimator 400.

Figure 2:
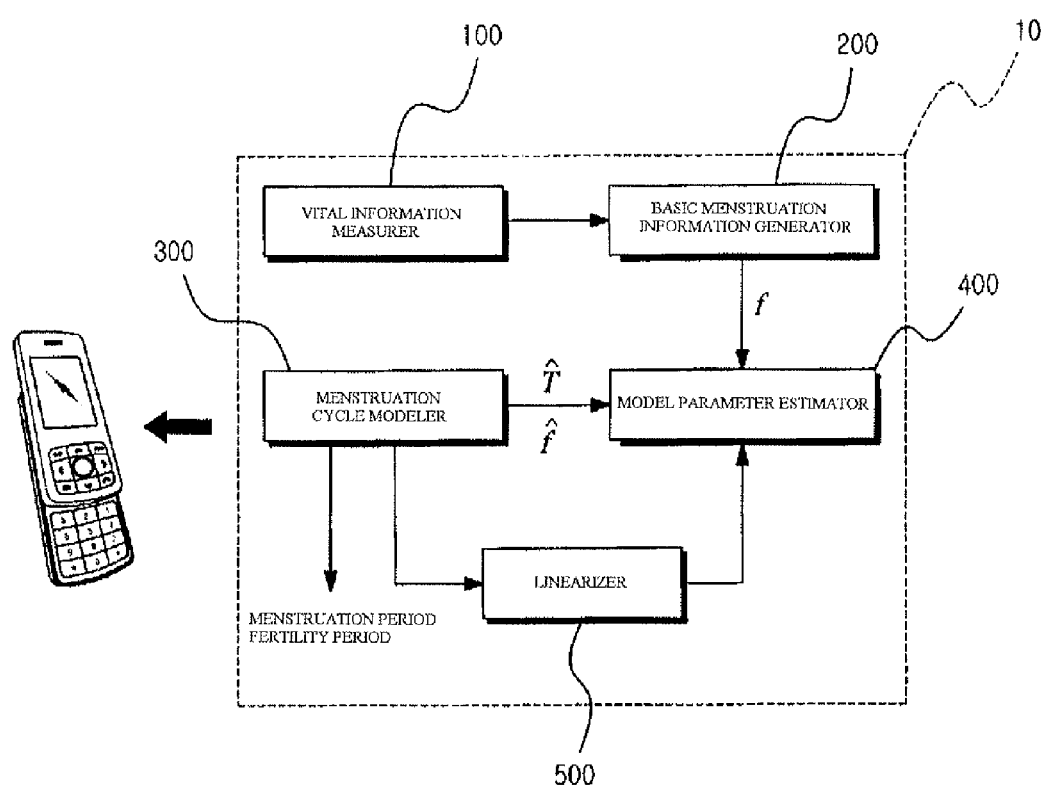
FIG. 2 illustrates a configuration of a mobile terminal equipped with a system for customized prediction of a menstruation period or fertility period according to another embodiment of the present invention.

FIG. 2 is a block diagram of a mobile terminal equipped with a system for customized prediction of a menstruation period or a fertility period according to an embodiment of the present invention. Referring to FIG. 2, the mobile terminal, which is comprised of a power supply, an input portion, an operator and a display, has a customized menstruation or fertility period prediction system 10 including the vital information measurer 100, the basic menstruation information generator 200, the menstruation cycle modeler 300, the model parameter estimator 400, and the linearizer 500.

As mobile terminals that most women carry with them are equipped with the customized menstruation or fertility period prediction system 10, as illustrated in FIG. 2, they may readily acquire more accurate information about their menstruation or fertility periods that they should be aware of and need to control their conditions.

Moreover, since a mobile terminal is provided with a high-performance microprocessor, it may perform computations for the above-described menstruation cycle modeling and model parameter estimation and display menstruation cycle information on the display in various manners. Provisioning of menstruation period or fertility period information along with various information services through the mobile terminal leads to a better-quality service.

Figure 3:
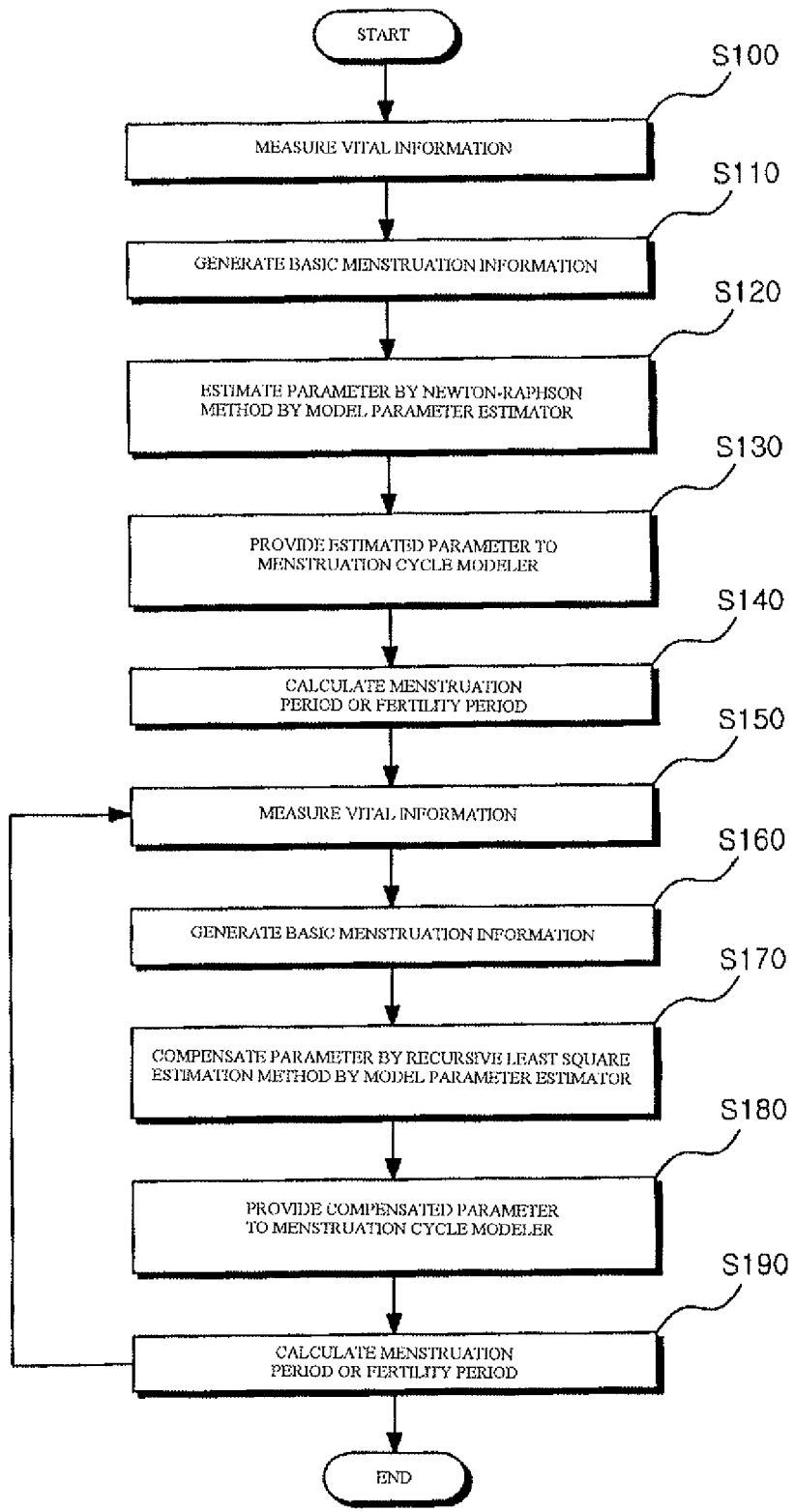
FIG. 3 is a flowchart illustrating a method for customized calculation of a menstruation period or fertility period according to the present invention.

FIG. 3 is a flowchart illustrating a method for customized calculation of a menstruation period or a fertility period according to the present invention.

Referring to FIG. 3, the vital information measurer 100 measures vital information such as hormone levels, temperature, etc. using a sensor attached to the mobile terminal in step S100. In step S110, the basic menstruation information generator 200 calculates basic menstruation information, i.e. the first day of menstruation or an ovulation day based on the vital information, or receives information indicating the first day of menstruation directly from the user.

The model parameter estimator 400 estimates a menstruation cycle parameter of a menstruation cycle model by the Newton-Raphson method in step S120 and provides the estimated menstruation cycle parameter to the menstruation cycle modeler 300 in step S130.

In step S140, the menstruation cycle modeler 300 calculates and predicts a menstruation period or fertility period of the user using the received estimated parameter. In an embodiment of the present invention, it is assumed that the menstruation period lasts for four days, starting from the onset of menstruation and the fertility period lasts from four days before ovulation to two days after the ovulation in the menstruation or fertility period calculation. However, the lengths of the menstruation and fertility periods are variable and may be set differently during the calculation.

When the user additionally measures vital information such as hormone levels, temperature, etc. in step S150 and the vital information measurer 100 provides additional basic menstruation information based on the additional vital information to the model parameter estimator 400 in step S160, the model parameter estimator 400 compensates the last estimated parameter of the menstruation cycle model using a linearized menstruation cycle model received from the linearizer 500 and the additional basic menstruation information in step S170.

For the compensation of the menstruation cycle parameter, the model parameter estimator 400 uses the recursive least square estimation. The compensated parameter is provided to the menstruation cycle modeler 300 in step S180 and the menstruation cycle modeler 300 calculates and predicts a menstruation period and a fertility period in step S190.

As is apparent from the above description of the present invention, a menstruation period or a fertility period of a user that best matches the current status of the user can be calculated and predicted in a customized manner by estimating a parameter of a menstruation cycle model represented as a periodic function.

As the menstruation period or fertility period prediction method is based on hormone levels and temperature, the menstruation period or fertility period can be effectively calculated even when the user's menstruation cycle is not regular.

A portable terminal, such as a mobile terminal, into which the user can enter her basic menstruation information through an internal device can be provided. The terminal may provide a customized service in conjunction with other services to the user based on accurately predicted menstruation period or fertility period information.

While the present invention has been described above with reference to certain embodiments, many variations and modifications can be made within the scope of the present invention. For instance, while the Newton-Raphson method is used for parameter estimation in the embodiments of the present invention, any other parameter estimation method is also available, such as the steepest descent method.

Also, if a response from the menstruation cycled model is represented as a waveform having distinctive characteristics, a parameter may be estimated by Discrete Fourier Transform (DFT)-based waveform analysis. Meanwhile, any periodic function with a certain period, such as a sine function, a cosine function, etc., may be used as the menstruation cycle mode. The menstruation cycle model may be expressed as a first-order linear algebraic equation. In this case, a slope corresponding to the coefficient of a first-order term is estimated as the parameter.

While the forgetting factor $\beta$ is given as equation (3) in the embodiments of the present invention, it may be represented as another formula that gives a small weight to old information data. Further, the recursive least square estimation method is used for the parameter compensation based on new basic menstruation information in the embodiments of the present invention. Yet, any other status estimator including a Kalman filter may be used, instead.

While every basic menstruation information from the basic menstruation information generator is used for parameter estimation in the embodiments of the present invention, the number of data used for the parameter estimation may be maintained constant by deleting old data, or a parameter that minimizes the target function value of equation (2) may selected from among a predetermined set of integers received as menstruation cycle estimates, or the like, in order to reduce computation volume.

In the embodiments of the present invention, vital information such as temperature and menstruation hormones including estrogen, progesterone, follicle stimulating hormone, luteinzing hormone, etc. are used for basic menstruation information generation. Apart from them, other vital information that varies in relation to a menstruation cycle, such as the amount of skin fluid or waste, may be used.

Also, a menstruation period or a fertility period may be predicted and calculated by a user's direct entry of the first day of menstruation or an ovulation day to the proposed system without the aid of the basic menstruation information generator. While the customized menstruation or fertility period prediction system is applied to a portable terminal like a mobile terminal in the embodiments of the present invention, it may also be applied to other equipment including medical equipment.

Embodiments of the present invention can also be embodied as computer-readable programs or a computer-readable recording medium with the programs as well as the above-described apparatus and method. This implementation can be easily construed as within the scope of the invention by programmers skilled in the art to which the present invention pertains.

While the invention has been shown and described with reference to certain exemplary embodiments, it will be understood by those skilled in the art that various changes in form and details may be made therein without departing from the spirit and scope of the present invention as defined by the appended claims and their equivalents.

What is claimed is:

1. A system for customized prediction of a menstruation period or a fertility period, comprising:
   a vital information measurer for measuring vital information about a user;
   a basic menstruation information generator for calculating the first day of menstruation or an ovulation day using the vital information received from the vital information measurer and outputting the first day of menstruation or the ovulation day as basic menstruation information;
   a menstruation cycle modeler having a non-linear menstruation cycle model representing a menstruation cycle as a function with a predetermined period;
   a linearizer for linearizing the non-linear menstruation cycle model of the menstruation cycle modeler and outputting a linearized menstruation cycle model; and
   a model parameter estimator using the linearized menstruation cycle model output from the linearizer for estimating and compensating a menstruation cycle parameter of the menstruation cycle model using the basic menstruation information received from the basic menstruation information generator.

2. The system of claim 1, wherein the vital information measurer comprises a sensor for measuring a variation in one of blood, sweat, and temperature of the user.

3. A mobile terminal having a power supply, an input portion, an operator and a display, comprising a system for customized prediction of a menstruation period or a fertility period, wherein the system comprises:
   a vital information measurer for measuring vital information about a user;
   a basic menstruation information generator for calculating the first day of menstruation or an ovulation day using the vital information received from the vital information measurer and outputting the first day of menstruation or the ovulation day as basic menstruation information;
   a menstruation cycle modeler having a non-linear menstruation cycle model representing a menstruation cycle as a function with a predetermined period; and
   a linearizer for linearizing the non-linear menstruation cycle model of the menstruation cycle modeler and outputting a linearized menstruation cycle model; and
   a model parameter estimator using the linearized menstruation cycle model output from the linearizer for estimating and compensating a menstruation cycle parameter of the menstruation cycle model using the basic menstruation information received from the basic menstruation information generator.

4. The mobile terminal of claim 3, wherein the vital information measurer comprises a sensor for measuring a variation in one of blood, sweat, and temperature of the user.

5. A method for customized calculation of a menstruation period or a fertility period, comprising:
   measuring vital information about a user by a vital information measurer;
   calculating the first day of menstruation or an ovulation day using the vital information received from the vital information measurer and outputting the first day of menstruation or the ovulation day as basic menstruation information;
   providing, in a menstruation cycle modeler, a non-linear menstruation cycle model representing a menstruation cycle as a function with a predetermined period;
   linearizing, in a linearizer, the non-linear menstruation cycle model and outputting a linearized menstruation cycle model;
   estimating, in a model parameter estimator, a model parameter indicating a menstruation cycle, the model parameter estimator using the linearized menstruation cycle model output from the linearizer and using the basic menstruation information; and
   calculating a menstruation period or a fertility period of the user using the estimated model parameter.

6. The method of claim 5, wherein the model parameter estimation is carried out by the Newton-Raphson method.

7. The method of claim 5, wherein the Newton-Raphson method uses the following model parameter estimation equation:

$$\hat{T} = \operatorname{argmin} \sum_{k=1}^{N} \beta(k) \left[ f(T; t_k) - \hat{f}(\hat{T}; t_k) \right]^2$$

subject to $$\hat{T}_{min} \leq \hat{T} \leq \hat{T}_{max}$$

where $\hat{T}$ denotes the parameter representing a menstruation cycle, $t_k$ denotes the first day of a $k^{th}$ menstruation or a $k^{th}$ ovulation day, $\hat{f}(\hat{T}; t_k)$ denotes a function value of a periodic function $\hat{f}$ that the menstruation cycle modeler calculates for time $t_k$, and $\beta$ is a forgetting factor.

8. The method of claim 5, wherein the model parameter estimation is carried out using the steepest descent method.

9. The method of claim 5, wherein the menstruation cycle of the menstruation cycle model is estimated based on previously received vital information about the user by the model parameter estimator.

10. The method of claim 9, wherein the model parameter estimation comprises compensating the model parameter by the recursive least square estimation method.

11. The method of claim 10, wherein the recursive least square estimation method uses the following model parameter compensation equation:

$$\hat{T}(N) = \hat{T}(N-1) + R^{-1}(N)\phi(N)\left(f(N) - \phi^T(N)\hat{T}(N-1)\right)$$

$$R(N) = \lambda(N)R(N-1) + \phi(N)\phi^T(N)$$

where $$R(N) = \sum_{k=1}^{N} \beta(k)\phi(k)\phi^T(k)$$

where $\hat{T}$ denotes the parameter representing a menstruation cycle, $\phi$ denotes a linearized menstruation cycle model, and $\beta$ is a forgetting factor.

* * * * *

UNITED STATES PATENT AND TRADEMARK OFFICE
CERTIFICATE OF CORRECTION

PATENT NO. : 8,374,989 B2
APPLICATION NO. : 12/579831
DATED : February 12, 2013
INVENTOR(S) : Lee et al.

Page 1 of 1

It is certified that error appears in the above-identified patent and that said Letters Patent is hereby corrected as shown below:

In the Specifications:

Column 3,
Line 38, in the equation "argmin" should read --arg min--.

Column 5,
Line 50, in the equation "argmin" should read --arg min--;
Line 57, "2, . . . N," should read --2, . . ., N,--.

In the Claims:

Column 9,
Line 39, "period; and" should read --period;--.

Column 10,
Line 22, "argmin" should read --arg min--.

Signed and Sealed this
Twentieth Day of August, 2013

Teresa Stanek Rea
*Acting Director of the United States Patent and Trademark Office*